United States Patent [19]

Schuster et al.

[11] Patent Number: 5,357,952
[45] Date of Patent: Oct. 25, 1994

[54] MEDICAL TUBE AND TUBE CONNECTOR RETENTION DEVICE

[75] Inventors: Michael Schuster, Malvern; Frank Nocella, Upper Holland, both of Pa.

[73] Assignee: Zipper Medical Products, Inc., Malvern, Pa.

[21] Appl. No.: 28,426

[22] Filed: Mar. 9, 1993

[51] Int. Cl.⁵ .................... A61M 16/00; A62B 9/02; A62B 9/06

[52] U.S. Cl. ................. 128/207.17; 128/912; 128/DIG. 26

[58] Field of Search ............ 128/207.14, 207.17, 128/207.11, DIG. 15, DIG. 26, 911, 912, 205.25

[56] References Cited

U.S. PATENT DOCUMENTS

| | | | |
|---|---|---|---|
| 1,592,345 | 7/1926 | Dräger | 128/207.17 |
| 2,928,387 | 3/1960 | Layne | 128/207.11 |
| 3,086,529 | 4/1963 | Munz et al. | 606/203 |
| 3,535,719 | 10/1970 | Murcott | 5/424 |
| 3,927,676 | 12/1975 | Schultz | 128/207.17 |
| 3,946,742 | 3/1976 | Eross | 128/207.17 |
| 3,987,798 | 10/1976 | McGinnis | 128/207.17 |
| 4,018,221 | 4/1977 | Rennie | 128/DIG. 26 |
| 4,027,666 | 6/1977 | Marx | 128/165 |
| 4,088,136 | 5/1978 | Hasslinger et al. | 128/349 |
| 4,246,897 | 1/1981 | Muto | 128/207.15 |
| 4,313,437 | 2/1982 | Martin | 128/207.17 |
| 4,331,144 | 5/1982 | Wapner | 128/207.17 |
| 4,527,559 | 7/1985 | Roxberg et al. | 128/207.17 |
| 4,548,200 | 10/1985 | Wapner | 128/207.17 |
| 4,738,662 | 4/1988 | Kalt et al. | 128/DIG. 15 |
| 4,838,867 | 6/1989 | Kalt et al. | 604/180 |
| 4,844,061 | 7/1989 | Carroll | 128/DIG. 26 |
| 5,101,822 | 4/1992 | Kimmel | 128/207.14 |

*Primary Examiner*—Kimberly L. Asher
*Attorney, Agent, or Firm*—Cushman, Darby & Cushman

[57] ABSTRACT

A medical tube retention device for securing a tube to a patient. The device is comprised of a band having interior and exterior surfaces and an elastic portion. At least a portion of the exterior surface has a first type of textile fastener covering. A first complementary textile fasting strip is affixed to one end of the band, and a second complementary textile fastening strip is releasably affixed to the opposite end. The textile fastening strips are attached to a tracheostomy or endotracheal tube flange through slots located on opposite sides of the flange. An optional third complementary textile fasting strip, affixed to the first end of the band, is secured to a tube connector and releasably affixed to the opposite end of the band to positively retain the connector to the tube.

5 Claims, 2 Drawing Sheets

MEDICAL TUBE AND TUBE CONNECTOR RETENTION DEVICE

BACKGROUND OF THE INVENTION

1. Field of the Invention

The present invention relates to a device for securing a medical tube to a patient. More particularly, it relates to a device for securing a tracheostomy tube or an endotracheal tube. Most particularly, the present invention provides a device for securing a tracheostomy or endotracheal tube to a patient and for positively retaining a ventilator tube connector to the tube.

2. Description of the Prior Art

Tracheostomy or endotracheal tubes are often placed in severely injured or ill patients to assist them in breathing. In many instances, a ventilator is connected to the tube to provide controlled ventilation.

Tracheostomy and endotracheal tubes were customarily supported in place by a thin cotton tape extending about the neck or head of a patient. The cotton tape was typically tied to slotted flanges on either side of the tube to secure it in place. This method for securing a tracheostomy or endotracheal tube has many drawbacks. The cotton tape had to be threaded through and knotted to each flange or separate pieces had to be threaded through the flanges and then tied to each other to secure the tube. There was no convenient means for securing and/or adjusting the cotton tape to ensure a proper fit. This could result in a poorly secured or mislocated tracheostomy tube, contributing to the potential for injury of the soft tissues surrounding the stoma of a tracheostomy.

The cotton tape utilized to secure the tube also has a tendency to stretch more at the edges than at the center as it is being installed, and the tying process further distorts the tape. This results in an uneven force distribution across the width of the tape causing patient discomfort and possible skin irritation. This condition is evidenced by the typical curl at the edges of the cotton tape. Additionally, there is not enough give in the cotton tape to accommodate expansion of the patient's neck due to swelling or coughing. If the patient's neck contracts, the tube must be resecured.

Because of the degree of intensive care required in using tracheostomy or endotracheal tubes, ease in maintaining the tracheostomy tube through adjustment or replacement of the retention means is also a prime concern. Not only must the retention means be easy to install and adjust, but asepsis concerns make it desirable that the retention means be low cost and therefore disposable.

U.S. Pat. No. 4,313,437 to Martin, issued Feb. 2, 1982, and U.S. Pat. No. 4,331,144 to Wapner, issued May 25, 1982 have attempted to address some of these problems. Both show the use of a padded foam neck band and VELCRO® fastening means. These provide easier installation, replacement and adjustment as well as more even force distribution and patient comfort. Although the tube retainer disclosed by Martin does provide for some expansion or contraction once installed, it has limited adjustability and several sizes are required for different size patients.

The support provided by Wapner involves a more complex structure. It utilizes two straps, one of which has an elastic webbing portion. This is to allow the attendant applying the band to select a comfortable pressure for securing the band to the patient. Because of its more complex structure, this support band is more costly to manufacture.

U.S. Pat. No. 5,101,822 to Kimmel, issued Apr. 7, 1992, also attempts to address these problems. Kimmel discloses a two-piece collar system which appears complex and requires the alignment of snaps on the two collar pieces and threading tapes from one collar piece through loops in the other for installation. This more complex structure could increase the cost of the device making disposable usage cost prohibitive.

None of these devices provide a means for positively retaining a ventilator tube connector to the tracheostomy or endotracheal tube in order to prevent inadvertent disconnection.

It is an object of this invention to provide an adjustable band for securing tracheostomy, endotracheal, or other medical tubes to a patient.

It is an object of this invention to provide a medical tube support band with means affixed to the band for releasably securing a connector to the tube.

It is an object of this invention to provide a disposable means for securing a tube to a patient.

These and other objects of the invention will be better understood and appreciated from the detailed description of the preferred embodiments of the invention which follow.

SUMMARY OF THE INVENTION

The present invention provides a tube retention device for securing a tube to a patient. The tube retention device is comprised of a band having interior and exterior surfaces and an elastic portion, with at least a portion of the exterior surface having a first type of textile fastener covering. A first complementary textile fastener strip is affixed to one end of the band and a second complementary textile fastening strip is releasably affixed to the opposite end of the band. The textile fastening strips are attached to a tracheostomy or an endotracheal tube flange through slots located on opposite sides of the flange. A means for releasably securing a connector to the tube can be affixed to one end of the band.

DESCRIPTION OF THE PREFERRED EMBODIMENTS

Figure 1:
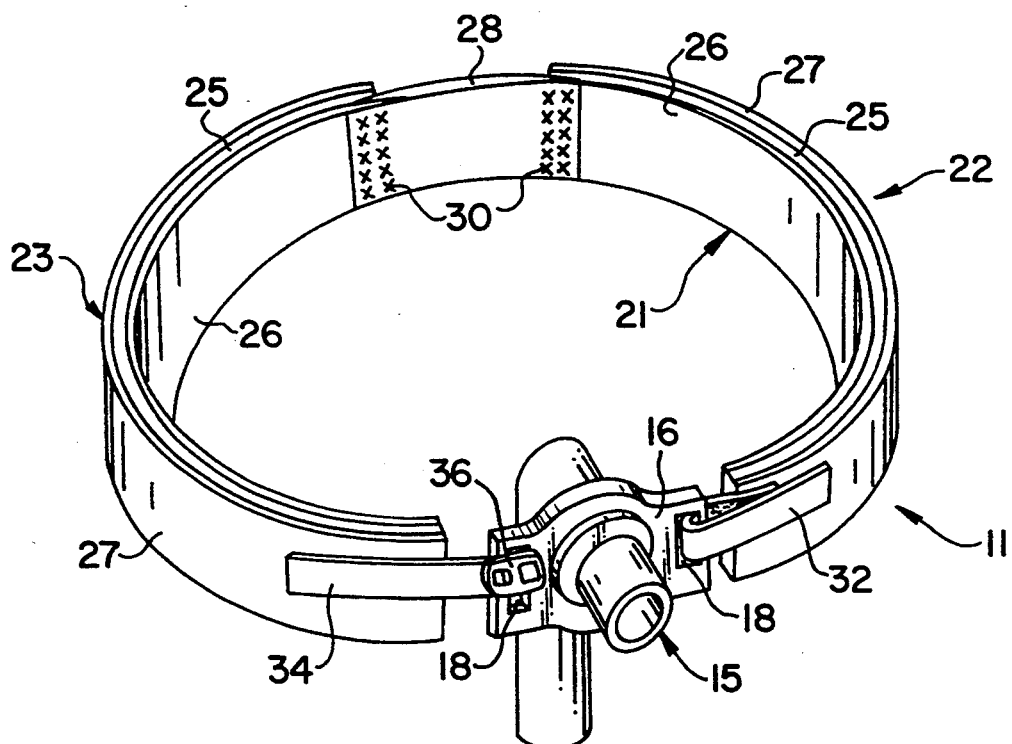
FIG. 1 is a perspective view of a first embodiment of the invention.

The preferred embodiments will be described with reference to the drawing figures wherein the same numeral indicates a like element throughout. Although the description will be made with reference to a tracheostomy tube, it will be appreciated by those skilled in the art that it applies equally to other medical tubes.

Referring to FIG. 1, there is shown a first embodiment 11 of the tube retention device according to the present invention. The tube retention device 11 is comprised of a band 21 made from two multi-layered portions 22 and 23 which are joined together by an elastic portion 28 along seams 30. Each multi-layered portion 22 and 23 consist of a foam sponge layer 25 which is located between interior and exterior layers 26 and 27. The interior layer 26 is a cotton fiber lining which will lay against the patient's skin to prevent irritation. In the preferred embodiment, the exterior layer 27 is made from a first type of textile fastener material such as a loop type textile fastening material sold under the trademark VELCRO ®. The elastic portion 28 can be made of an elastic material such as VELSTRETCH. The seams 30 connecting the two multi-layered portions 22 and 23 can be formed by heat staking or conventional stitching, depending on the materials used. The band 21 is approximately 1- inch wide and its overall length is approximately 18 inches. The elastic portion 28 is approximately 1.5 inches long, or 8–10% of the total band length.

Affixed to one end of the band 21 is a first complementary textile fastening strip 32. The fastening strip is a hook-type textile fastening strip which is complementary to the loop-type textile fastening strip of exterior layer 27. One end of this fixed hook type textile fastening strip 32 is permanently attached to the first end of the band 21. As will be recognized by those skilled in the art, the band 21 is placed around the patient's neck, and the length of the band 21 is adjusted by trimming the end opposite from the first complementary textile fastening strip 32. The free end of the first complementary textile fastening strip 32 is then passed through a slot 18 in the flange 16 of the tracheostomy tube 15, and doubled back to a position above the loop-type textile fastening material of the exterior layer 27 where it is releasably secured.

A second complementary textile fastening strip 34 with a buckle 36 affixed to one end is threaded through the opposite slot 18 on flange 16. The second complementary textile fastening strip is made of a hook-type textile fastening material which is complementary to exterior layer 27. The second complementary textile fastening strip 34 is then releasably affixed to the loop type textile fastening material of the exterior cover 27 on the opposite end of band 21 from the fixed textile fastening strip 32, securing the tracheostomy tube 15 in position. The textile fasting strip 34 does not have to be threaded through the buckle 36 in order to secure the textile fastening strip 34 to the flange 16. The buckle 36 is of sufficient size so that it cannot pass through the slot 18. Both the fixed and removable textile fastening strips 18 are approximately 0.4 inches wide and 3.5 inches long.

The length of the band 21 can be adjusted by trimming the end to which the removable textile fastening strip 34 will be secured prior to its installation. Therefore, the medical tube retention device 11 can be produced in a single size and be trimmed during installation to provide a custom fit for each patient.

As will be recognized by those skilled in the art, the elastic portion 28 of the band 21 will allow for some expansion of the patient's neck due to swelling or coughing.

Figure 2:
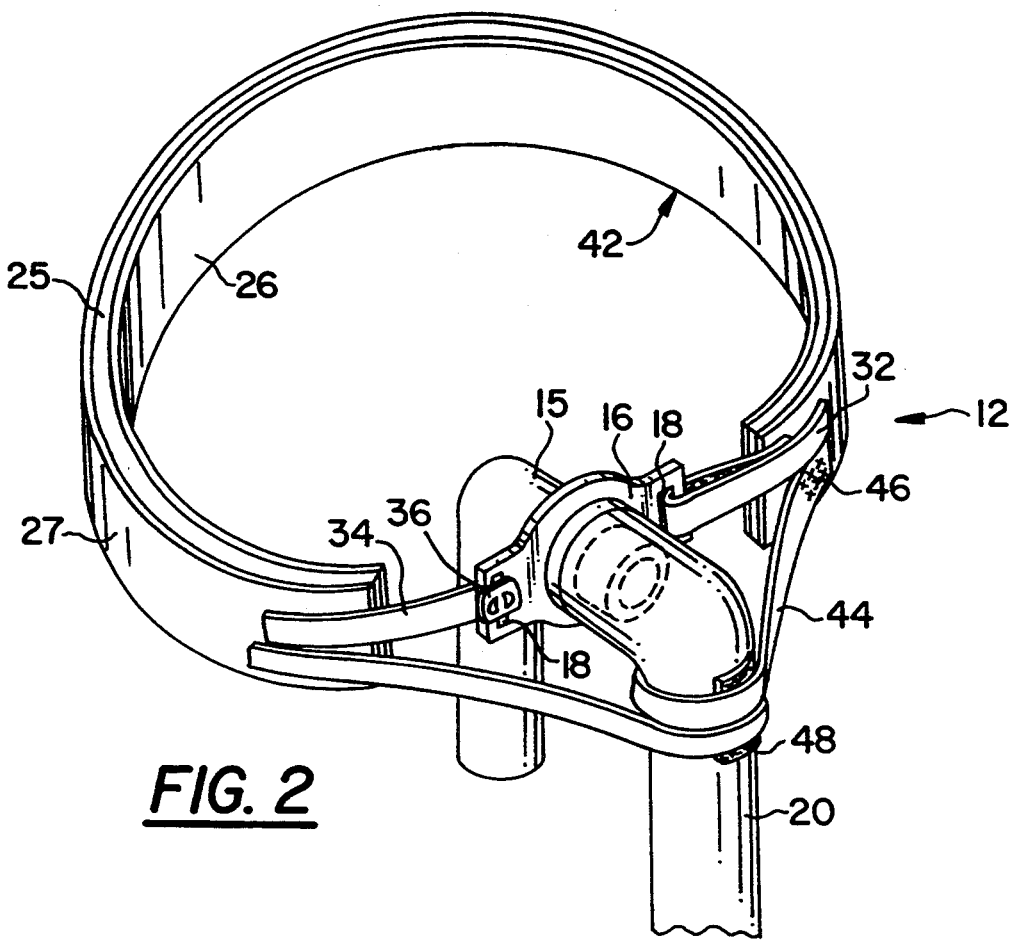
FIG. 2 is a perspective view of a second embodiment of the invention including means for releasably retaining a connector to the tube.

A second embodiment of the tube retention device 12 including a tube connector retaining means is shown in FIG. 2. As is known in the art, a ventilator connector 20 is frequently attached to the tracheostomy or endotracheal tube 15 to assist the patient in breathing. In order to prevent the ventilator connector from being inadvertently dislodged, a means for positively retaining the connector 20 to the tracheostomy tube 15 is incorporated into the medical tube retention device 12. The device 12 is comprised of a multi-layered band 42 having a layer of foam sponge material 25 located between interior and exterior layers 26 and 27, as previously described.

A first complementary textile fastening strip 32 is affixed to a first end of the band 42 and a second complementary textile fastening strip 34 is releasably secured to the opposite end of the band 42. A third complementary textile fastening strip 44 is affixed by seam 46 to the first end of the band 42 in a position adjacent to the first complementary textile fastening strip 32. This third textile fastening strip is approximately 14 inches long and is made of a hook-type textile fastening material.

In use, the length of the band is adjusted, and the fixed and removable textile fastening strips 32 and 34 are attached through the slots 18 in the flange 16 on tracheostomy tube 15 in the manner previously described. When a ventilator tube connector 20 is attached to the tracheostomy tube 15, a patch of pile type textile fastening material 48 with an adhesive backing is affixed to the connector 20. The connector retaining textile fastening strip 44 is then releasably affixed to the patch 48, wrapped around the connector 20 until it again contacts the patch 48, and then its free end is secured to the band 42 in a position adjacent to the removable textile fastening strip 34. This provides a positive means for retaining the ventilator tube connector 20 to the endotracheal tube 15.

Figure 3:
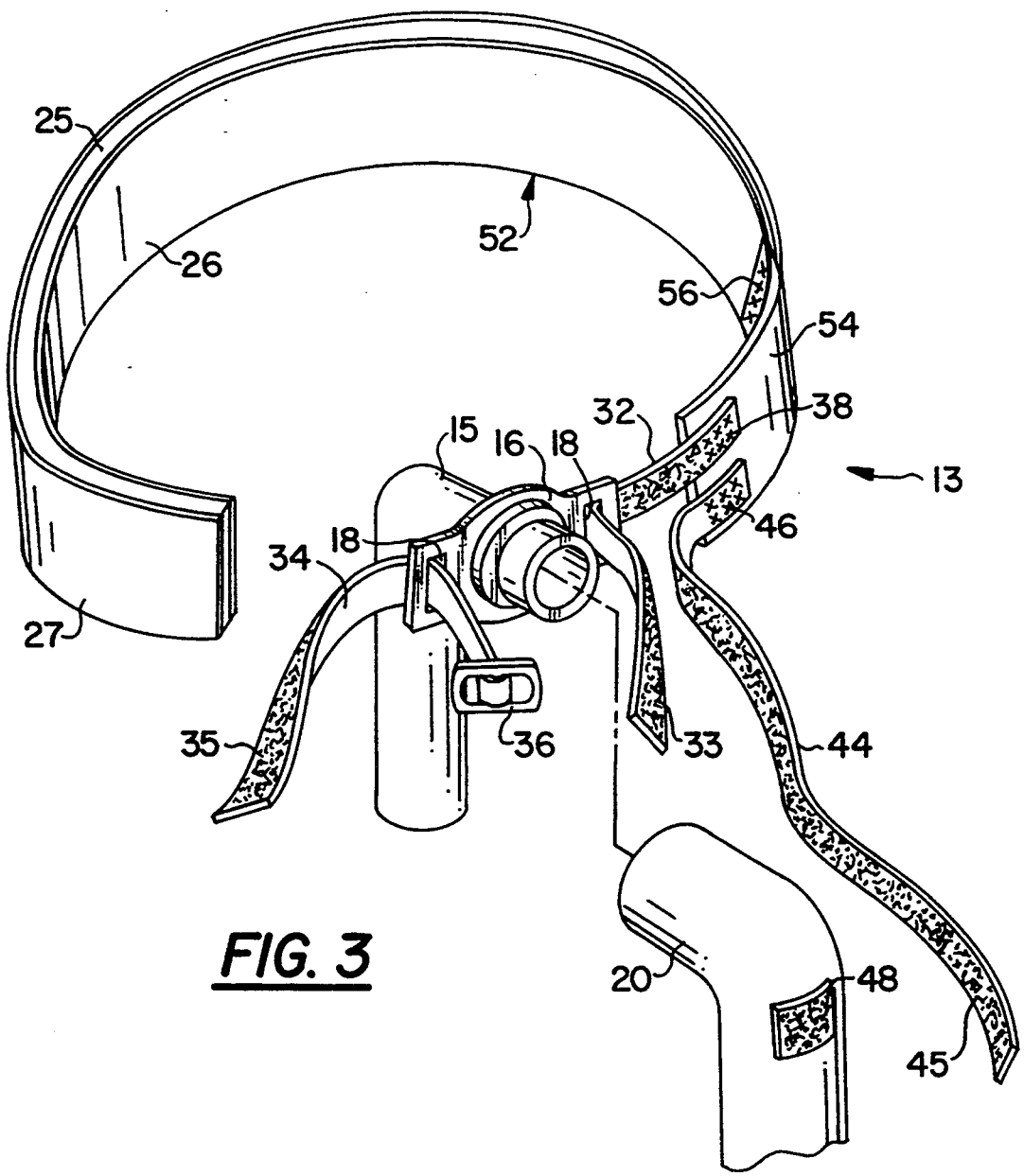
FIG. 3 is a partially assembled perspective view of a third embodiment of the invention including means for releasably retaining a tube connector.

A third embodiment of the invention 13 is shown in FIG. 3. This third embodiment of the invention 13 is similar to the second embodiment of the invention 12. In order to provide a clearer understanding of the invention, the first and second complementary textile fastening strips 32 and 34 are shown partially installed, and the connector 20 is removed from the tube 15.

The band 52 is similar to band 42 and is comprised of a layer of foam sponge material 25 located between interior and exterior layers 26 and 27 as previously described. Affixed to a first end of the band 52 is an elastic portion 54. The elastic portion 54 can be heat staked or attached by conventional stitching to the first end of the band along seam 56. The first complementary hook type textile fastening strip 32 is affixed by seam 38 to the free end of the elastic portion 54, and is positioned such that its hooks 33 face outward from the band 52. A third complementary connector retaining textile fastening strip 44 is affixed by seam 46 to the free end of the elastic portion 54 adjacent to the first complementary textile fastening strip 32. The third complement connector retaining textile fastening strip 44 is positioned such that its hooks 45 face toward the band 52.

The third embodiment of the invention 13 is installed in a similar manner to the second embodiment 12, as previously described. As illustrated in FIG. 3, the second complementary textile fastening strip 34 is installed through the slot 18 such that the hooks 35 face toward the exterior layer 27 of the band 52. The elastic portion 54 allows for some expansion of the patient's neck due to swelling or coughing.

Figure 4:
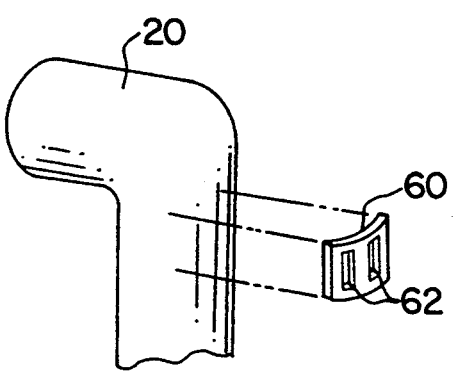
FIG. 4 is a perspective view illustrating an alternate connector retention configuration.

Referring to FIG. 4, an alternate configuration for the adhesive backed connector retaining patch 60 is shown. A pair of parallel slots 62 are formed in the patch 60. The connector retaining textile fastening strip 44 is threaded through the slots 62 in the patch 60 during installation. The patch is then applied to the connector 20.

Figure 5:
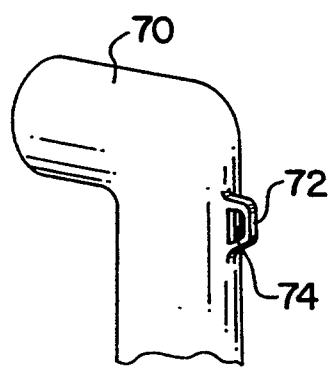
FIG. 5 is a perspective view illustrating an alternate connector configuration which can be utilized in conjunction with the present invention.

An alternate configuration for the connector 70 is shown in FIG. 5 which eliminates the need for a connector retaining patch. A loop 72 is formed on the connector 70 creating an aperture 74 of sufficient size for the connector retaining textile fastening strip 44 to pass through during installation. For the preferred embodiments, the aperture 74 is approximately 0.5 inches wide and 0.2 inches high.

The foregoing invention has been described with specific reference to the preferred embodiments; however, it will be appreciated that modifications can be made without departing from the scope of the invention. It will also be appreciated by those skilled in the art that the complementary fastening strips 32, 34 and 44 are secured to exterior layer 27. Although the preferred embodiments have been described with specific reference to hook and pile textile fastening material, other textile fastening materials are within the scope of the present invention.

We claim:

1. A device for securing a medical tube comprising a tracheostomy or endotracheal tube and a slotted flange having a first and a second slot, said device positively retaining the medical tube to a ventilator tube connector, the device comprising:
   a band, having an exterior surface, a first and a second end, the exterior surface including a first type of textile fastening material;
   a first fastening strip having at least a portion of an interior surface that is complementary to the first type of textile fastening material and is releasably affixed to the first end of the band, the first fastening strip being releasably connected to the first slot of the slotted flange;
   a second fastening strip having at least a portion of an interior surface that is complementary to the first type of textile fastening material and is affixed to the second end of the band, the second fastening strip being releasably connected to the second slot of the slotted flange;
   a third fastening strip having at least a portion of an interior surface that is complementary to the first type of textile fastening material, the third fastening strip being affixed to the second end of the band and releasably the first end of the band; and
   means for attaching the ventilator tube connector to the third fastening strip, said means for attaching comprising a loop formed on the ventilator tube connector;
   the third fastening strip, in a securing position, connected to said second end of said band, to said means for attaching, and to said first end of said band.

2. A medical tube retention device for securing a medical tube comprising a tracheostomy or endotracheal tube, said device securing a ventilator tube connector to the medical tube, the device comprising:
   a band having an exterior surface, a first end and a second end; at least a portion of the exterior surface of the band including a first type of textile fastener;
   a first textile fastening strip complementary to the first type of textile fastener, having a first end releasably affixed to the first end of the band and having a second end secured to the medical tube;
   a second textile fastening strip complementary to the first type textile fastener, affixed to the second end of the band and releasably secured to the medical tube;
   a third textile fastening strip complementary to the first type textile fastener, affixed to the second end of the band and releasably secured to the first end of the band; and
   means for attaching the ventilator tube connector to the third fastening strip, said means for attaching comprising a patch of attachment material secured to the ventilator tube connector;
   the third fastening strip, in a securing connected to said second end of said band, said patch of attachment material secured to said ventilator tube connector, and to said first end of said band.

3. The device according to claim 2, wherein said patch is an adhesive backed patch of the first type textile fastening material.

4. The device according to claim 2, wherein said patch of attachment material has a pair of parallel slots formed therein, and said third fastening strip is connected to said patch upon insertion through said slots.

5. A device to be used in connection with a medical tube comprising a tracheostomy or endotracheal tube of the type having an attachment flange with a first and second slot defined therein, said device positively retaining a ventilator tube connector connected to the medical tube, the device comprising:
   a band for wrapping around a portion of a patient's anatomy, the band having an exterior surface, a first end and a second end, and at least a portion of the exterior surface which is adjacent to the first and at least a portion of the exterior surface which is adjacent to the second end both include a first type of textile fastener;
   a first textile fastening strip complementary to the first type of textile fastener having a first end secured to the first slot in the flange and a second end affixed to the first end of the band;
   a second textile fastening strip complementary to the first type of textile fastener having a first end secured to the second end of the band and a second end looped through the second slot in the flange and releasably affixed to the second end of the band; and
   ventilator tube connector securing means affixed to the band for positively retaining the ventilator tube connector to the medical tube, the ventilator tube connector securing means comprising:
      i.) a third textile fastening strip complementary to the first type of textile fastener affixed to the second end of the band; and
      ii.) a strip of attachment material connected to the ventilator tube connector and received, when in a securing position, by the third textile fastening strip;
   wherein the first and second textile fastening strips secure the medical tube to the patient; and
   wherein the ventilator tube connector securing means prevents an accidental dislodgement of the ventilator tube connector from the medical tube.

* * * * *